United States Patent [19]

Nakanishi et al.

[11] 3,931,205

[45] Jan. 6, 1976

[54] SUBSTITUTED ALKANOIC ACIDS AND DERIVATIVES

[75] Inventors: Michio Nakanishi; Takanori Oe, both of Oita; Mineo Tsuruda, Fukuoka, all of Japan

[73] Assignee: Yoshitomi Pharmaceutical Industries, Ltd., Osaka, Japan

[22] Filed: July 18, 1973

[21] Appl. No.: 380,415

[30] Foreign Application Priority Data

July 21, 1972 Japan................................ 47-73679
July 21, 1972 Japan................................ 47-73680
Jan. 13, 1973 Japan................................ 48-6759
Jan. 13, 1973 Japan................................ 48-6760
Apr. 3, 1973 Japan................................ 48-38418

[52] U.S. Cl. ...... 260/295 T; 260/247.2; 260/290 R; 260/293.58; 260/294.8; 260/295.5 T; 260/297; 260/345.2; 424/248; 424/250; 424/263; 424/267; 424/274

[51] Int. Cl.² .................................... C07D 471/00

[58] Field of Search................... 260/295 T, 295.5 T

[56] References Cited
UNITED STATES PATENTS

| | | | |
|---|---|---|---|
| 3,429,889 | 2/1969 | Shulgin............................ | 260/295 T |
| 3,514,464 | 5/1970 | Pars et al. ....................... | 260/295 T |
| 3,583,997 | 6/1971 | Ebnother......................... | 260/295 T |
| 3,787,424 | 1/1974 | Pars et al. ....................... | 260/295 T |

OTHER PUBLICATIONS

*Chemical Abstract Subject Index,* 8th Collect, (1967–1971), p. 4369S–4370S.

*Primary Examiner*—Norman A. Drezin
*Attorney, Agent, or Firm*—Sughrue, Rothwell, Mion, Zinn, Macpeak

[57] ABSTRACT

Substituted alkanoic acids and derivatives thereof of the formula:

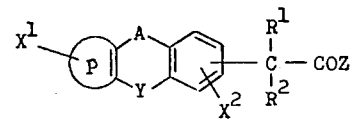

wherein each of $X^1$ and $X^2$ is a hydrogen atom, a halogen atom, an alkyl group having 1 to 4 carbon atoms or an alkoxy group having 1 to 4 carbon atoms; each of $R^1$ and $R^2$ is a hydrogen atom or an alkyl group having 1 to 4 carbon atoms; A is a carbonyl group, a methylene group or an alkylidene group having 2 to 4 carbon atoms; Y is —O—, —S— or —N(R)— [wherein R is a hydrogen atom or an alkyl group having 1 to 4 carbon atoms]; Z is OH or Q—B—N($R^3$)($R^4$) [wherein Q is O (oxygen atom) or NH, B is an alkylene group having 1 to 4 carbon atoms and each of $R^3$ and $R^4$ is a hydrogen atom or an alkyl group having 1 to 4 carbon atoms, or $R^3$ and $R^4$ together with the adjacent nitrogen atom form a saturated heterocycle selected from the group consisting of pyrrolidine, piperidine, morpholine, piperazine and piperazine substituted by an alkyl group having 1 to 4 carbon atoms at the 4-position]; and ring P represents a pyridine or a pyridine N-oxide ring; and pharmaceutically acceptable salts thereof are useful as antirheumatics, analgesics, antipyretics and anti-inflammatory agents.

18 Claims, No Drawings

SUBSTITUTED ALKANOIC ACIDS AND DERIVATIVES

This invention relates to novel and therapeutically valuable compounds of the formula:

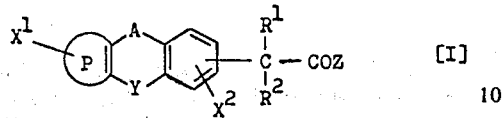   [I]

and pharmaceutically acceptable salts thereof, wherein each of $X^1$ and $X^2$ is a hydrogen atom, a halogen atom (e.g. F, Cl or Br), an alkyl group having 1 to 4 carbon atoms (e.g. methyl, ethyl, propyl or butyl) or an alkoxy group having 1 to 4 carbon atoms (e.g. methoxy, ethoxy, propoxy or butoxy); each of $R^1$ and $R^2$ is a hydrogen atom or an alkyl group having 1 to 4 carbon atoms (e.g. methyl, ethyl, propyl or butyl); A is a carbonyl group, a methylene group or an alkylidene group having 2 to 4 carbon atoms (e.g. ethylidene, propylidene, isopropylidene or butylidene); Y is —O—, —S— or —N(R)— [wherein R is a hydrogen atom or an alkyl group having 1 to 4 carbon atoms (e.g. methyl, ethyl, propyl or butyl)]; Z is OH or Q—B—N($R^3$)($R^4$) [wherein Q is O (oxygen a atom) or MH, B is an alkylene group having 1 to 4 carbon atoms (e.g. methylene, ethylene, trimethylene, propylene or tetromethylene) and each of $R^3$ and $R^4$ is a hydrogen atom or an alkyl group having 1 to 4 carbon atoms (e.g. methyl, ethyl, propyl or butyl), or $R^3$ and $R^4$ together with the adjacent nitrogen atom form a saturated hetorocycle selected from the group consisting of pyrrolidine, piperidine, morpholine, piperazine and piperazine substituted by an alkyl group having 1 to 4 carbon atoms at the 4-position (e.g. 4-methylpiperazine, 4-ethylpiperazine, 4-propylpiperazine or 4-butylpiperazine)], and ring P represents a pyridine or a pyridine N-oxide ring.

The ring system:

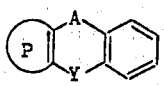

in the above formula represents one of the following (1)–(4).

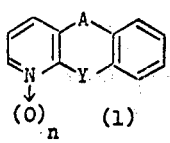 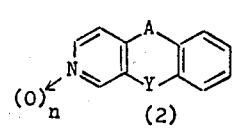

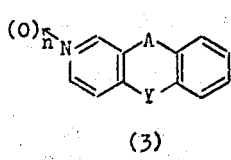 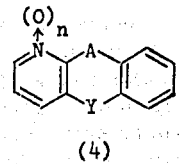

where $n = 0$ (zero) or 1. They are useful as antirheumatics, analgesics, antipyretics and anti-inflammatory agents.

The compounds of formula [I] can be produced, for example, by the following methods:

I. In the case of compounds of formula [I] wherein Z is OH;
a. By hydrolyzing a compound of the formula:

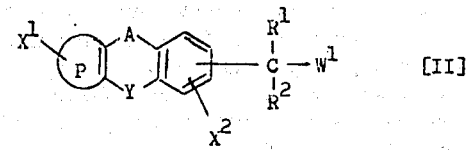   [II]

wherein $X^1$, $X^2$, $R^1$, $R^2$, A, Y and P are as defined above, and $W^1$ is a functional group hydrolyzable into COOH [e.g. COO$R^5$ (wherein $R^5$ is an alkyl group having 1 to 4 carbon atoms such as methyl, ethyl, propyl or butyl),

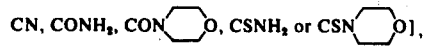

in a conventional manner.

The hydrolysis is advantageously carried out in a solvent (e.g. water, aqueous methanol, aqueous dioxane or acetic acid) in the presence of an acid (e.g. hydrochloric acid or sulfuric acid) or an alkali (e.g. sodium hydroxide or potassium hydroxide), usually under reflux.

b. By hydrolyzing and decarboxylating a compound of the formula:

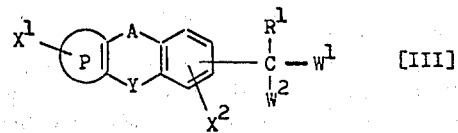   [III]

in a conventional manner, wherein $X^1 X^2$, $R^1$, A, Y, $W^1$ and P are as defined above, and $W^2$ is a functional group hydrolyzable into COOH [e.g. COO$R^5$ (wherein $R^5$ is as defined above),

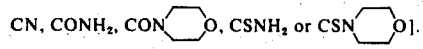

More particularly, the compound of formula [III] is hydrolyzed, advantageously under alkaline conditions with sodium hydroxide or potassium hydroxide, to give a corresponding malonic acid, and the thus-obtained malonic acid derivative is decarboxylated under neutral or acid conditions; or the compound of formula [III] is hydrolyzed and decarboxylated at the same time under acid conditions with hydrochloric or sulfuric acid. The reaction is usually carried out under reflux.

According to this method (b), the compound of formula [I] wherein $R^2$ is a hydrogen atom is obtained.

c. By oxidizing a compound of the formula:

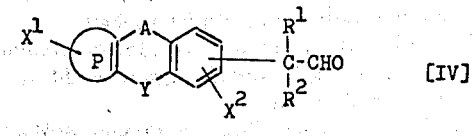   [IV]

wherein $X^1$, $X^2$, $R^1$, $R^2$, A, Y and P are as defined above.

The oxidation is advantageously carried out in a solvent (e.g. acetic acid, propionic acid, acetone, dioxane, water or a mixture of water and any of the said solvents) in the presence of an oxidizing agent (e.g. nitric acid, halogen, hydrogen peroxide, copper hydroxide, selenium dioxide, chromic anhydride, dichromate, permanganata, silver oxide, organic peracid or hypochlorous ester) at 0°–80°C.

d. By reducing a compound of the formula:

$$\text{[V]} \qquad \text{[VI]}$$

wherein $X^1$, $X^2$, $R^1$, $R^2$, Y and P are as defined above, and $R^6$ is a hydrogen atom or an alkyl group having 1 to 4 carbon atoms (e.g. methyl, ethyl, propyl or butyl), in a conventional manner.

The reduction of the compound of formula [V] gives directly the compound of formula [I] wherein A is a methylene group, or the compound of formula [VI] depending upon the starting material and/or the reduction conditions.

A conventional reduction, e.g. Wolff-Kishner reduction, Haung-Minlon modification thereof, Clemensen reduction, catalytic reduction under a catalyst such as nickel, palladium or platinum, reduction by the use of sodium borohydride or reduction by the use of of red phosphorus and hydriodic acid, can be applied. The compound of formula [VI] can also be reduced only by heating, advantageously in the presence of an acid, to give the compound of formula [I] wherein A is a methylene group.

The reduction is usually carried out in a solvent (e.g. methanol, ethanol, isopropyl alcohol, dioxane or water) at 10°–100°C for a period of from 1 to 10-odd hours.

According to this method (d), the compound of formula [I] wherein A is a methylene group is obtained.

e. By hydrogenating a compound of the formula:

$$\text{[VII]}$$

wherein $X^1$, $X^2$, A, Y and P are as defined above, and each of $R^7$ and $R^8$ is a hydrogen atom or an alkyl group having 1 to 3 carbon atoms (e.g. methyl, ethyl or propyl). The sum of carbon atoms of $R^7$ and $R^8$ is not more than 3.

A conventional hydrogenation, e.g. catalytic hydrogenation under a catalyst such as nickel, palladium or platinum of hydrogenation by the use of red phosphorus and hydriodic acid, can be applied.

According to this method (e), the compound of formula [I] wherein $R^1$ is an alkyl group and $R^2$ is a hydrogen atom is obtained.

f. By hydrogenolyzing a compound of the formula:

$$\text{[VIII]}$$

wherein $X^1$, $X^2$, $R^1$, A, Y and P are as defined above, and $W^3$ is a hydroxyl group, a halogen atom (e.g. Cl or Br) or a residue or an amine (e.g. dimethylamino, piperidino or morpholino).

A conventional hydrogenolysis, e.g. catalytic hydrogenolysis under a catalyst such as nickel, palladium or platinum, hydrogenolysis by the use of metal and acid (e.g. zinc-acetic acid) or hydrogenolysis by the use of red phosphorus and iodine, can be applied.

According to this method (f), the compound of formula [I] wherein $R^2$ is a hydrogen atom is obtained.

g. By reacting a compound of the formula:

$$\text{[IX]}$$

with carbon dioxide, wherein $X^1$, $X^2$, $R^1$, $R^2$, Y and P are as defined above, A' is a methylene group or an alkylidene group having 2 to 4 carbon atoms and $W^4$ is a lithium atom or a residue of a Grignard reagent.

According to this method (g), the compound of formula [I] wherein A is a methylene group or an alkylidene group is obtained.

h. By subjecting a compound of the formula:

$$\text{[X]}$$

to intramolecular condensation, wherein $X^1$, $X^2$, $R^1$, A and P are as defined above, either $Y^1$ or $Y^2$ is Y—H [wherein Y is as defined above], and the other is a halogen atom (e.g. Cl, Br or I).

The condensation is advantageously carried out in the presence of a hydrochloride or a sulfate or pyridine, quinoline or picoline at 100°–250°C.

i. By subjecting a compound of the formula:

$$\text{[XI]}$$

to intramolecular condensation, wherein $X^1$, $X^2$, $R^1$, $R^2$, Y and P are as defined above.

The condensation is carried out with or without a solvent (e.g. benzene, nitrobenzene or dichloroethane) in the presence of a condensing agent (e.g. polyphosphoric acid, phosphoric anhydride, sulfuric acid, aluminum chloride, acetic anhydride, boron trifluoride or hydrogen chloride) at about 20° to 150°C.

According to this method (i), the compound of formula [I] wherein A is a carbonyl group is obtained.

j. By reacting a compound of the formula:

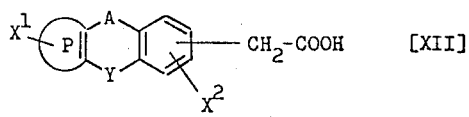

wherein $X^1$, $X^2$, A, Y and P are as defined above, with a compound of the formula:

$R^9 - Q^1$                          [XIII]

wherein $R^9$ is an alkyl group having 1 to 4 carbon atoms (e.g. methyl, ethyl, propyl or butyl), and $Q^1$ is a halogen atom (e.g. Cl, Br or I) or an alkyl- or aryl-sulfonyloxy (e.g. p-tolylsulfonyloxy or methylsulfonyloxy).

The reaction is advantageously carried out in an inert solvent (e.g. benzene, toluene, xylene, tetrahydrofuran, dimethyl sulfoxide or liquid ammonia) in the presence of an alkaline condensing agent (e.g. sodium methoxide, sodium ethoxide, sodium amide, potassium amide or sodium hydride) at about −35° to 150°C.

According to this method (j), the compound of formula [I] wherein $R^1$ is an alkyl group and $R^2$ is a hydrogen atom or the same alkyl group as $R^1$ is obtained.

II. In the case of compounds of formula [I] wherein Z is Q—B—N($R^3$)($R^4$);

k. By reacting a compound of the formula:

$Q^2 - B - N(R^3)(R^4)$                    [XIV]

wherein B, $R^3$ and $R^4$ are as defined above, and $Q^2$ is OH, $NH_2$, or a halogen atom (e.g. Cl or Br) or an alkyl- or aryl-sulfonyloxy (e.g. p-tolylsulfonyloxy or methylsulfonyloxy), with the compound of formula [I] wherein Z is OH or its reactive derivative appropriately selected.

The reactive derivative of the compound of formula [I] wherein Z is OH is, for example, a metal salt (e.g. sodium salt, potassium salt, calcium salt), an acid halide, an acid anhydride or a lower alkyl ester (e.g. methyl ester, ethyl ester, propyl ester or isopropyl ester).

The reaction is carried out in a conventional manner. For example, in the case of the reaction of the compound of formula [I] wherein Z is OH with the compound of formula [XIV] wherein $Q^2$ is OH or $NH_2$, the reaction is carried out in a solvent (e.g. benzene, toluene, xylene or chloroform), optionally in the presence of an acid catalyst such as sulfuric acid or p-toluenesulfonic acid.

l. By reacting a compound of the formula:

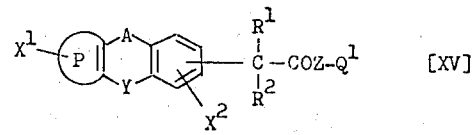

wherein $X^1$, $X^2$, $R^1$, $R^2$, A, Y, Z, B, $Q^1$ and P are as defined above, with a compound of the formula:

$HN(R^3)(R^4)$                    [XVI]

wherein $R^3$ and $R^4$ are as defined above.

The reaction is usually carried out in an inert solvent (e.g. benzene, toluene, acetone, dimethylformamide, dioxane or ethanol) at about 20° to 150°C, optionally in the presence of a condinsing agent (e.g. organic base such as pyridine, quinoline or picoline or inorganic base such as potassium carbonate or sodium carbonate).

The above starting compounds can be produced, for example, as follows:

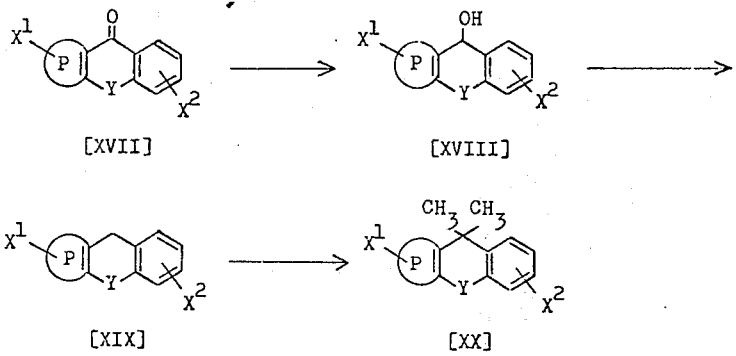

[XVII] is reduced to [XVIII], for example, by the method described in *Journal of the Chemical Society*, 1952, pages 2057–62; [XVIII] is heated in the presence of an acid to give [XIX]; [XIX] is methylated with methyl iodide in the presence of an alkalline condensing agent such as sodium amide to give [XX].

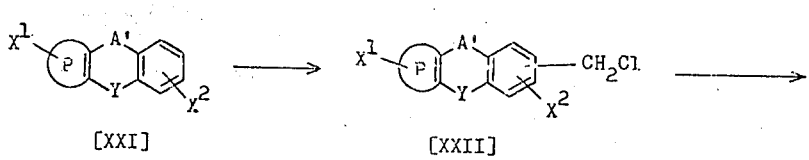

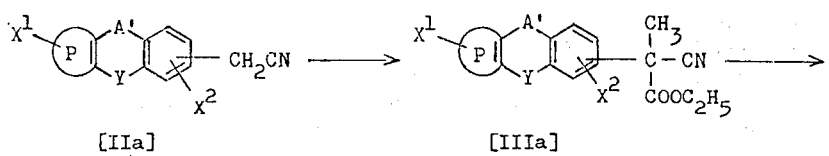

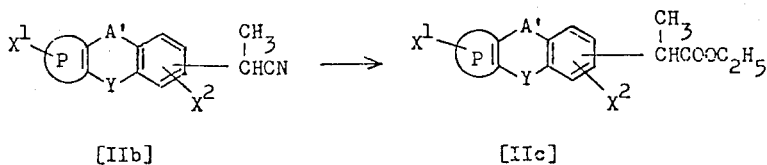

wherein A' is a methylene group or an alkylidene group having 2 to 4 carbon atoms.

[XXI] is chloromethylated with hydrogen chloride and formaldehyde to give [XXII]; [XXII] is allowed to react with potassium cyanide or cuprous cyanide in a solvent (e.g. dimethylformamide or dimethyl sulfoxide) to give [IIa]; [IIa] is allowed to react with diethyl carbonate and methyl iodide in the presence of sodium methoxide to give [IIIa]; [IIIa] is decarboxylated under reflux to give [IIb]; [IIb] is allowed to react with ethanol in the presence of a concentrated sulfuric acid to give [IIc].

[XXIII] is brominated with N-bromosuccinimide (N.B.S.) to give [XXIV]; [IId] and [IIIb] are derived from [XXIV] by the method mentioned above; methylation of [IId] with methyl iodide in the presence of an alkalline condensing agent gives [IIe].

[XXV] is acetylated with acetyl chloride or acetic anhydride in the presence of a catalyst such as anhydrous aluminum chloride to give [XXVI]; [XXVI] is subjected to Darzens' condensation to give [XXVII]; [XXVII] is hydrolyzed, and the resultant acid is decarboxylated by heating in an aqeuous or alcoholic solvent in the presence of an acid to give [IVa].

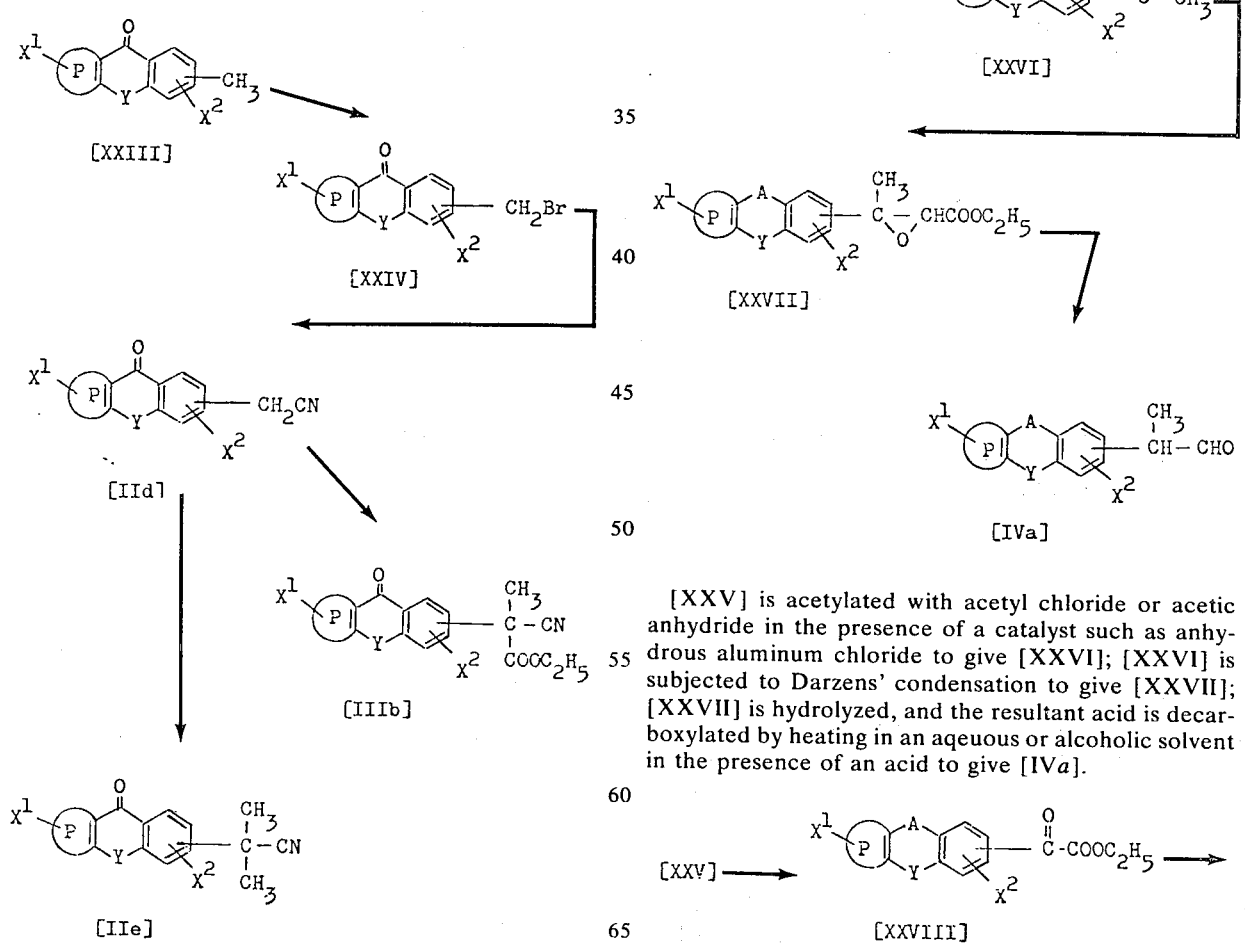

[VIIIa] → [VIIa]

[XXV] is allowed to react with ethoxalyl chloride in the presence of aluminum chloride to give [XXVIII]; [XXVIII] is hydrolyzed, and the resultant acid is subjected to Grignard reaction with methyl magnesiumm iodide to give [VIIIa]; [VIIIa] is dehydrated with sulfuric acid to give [VIIa].

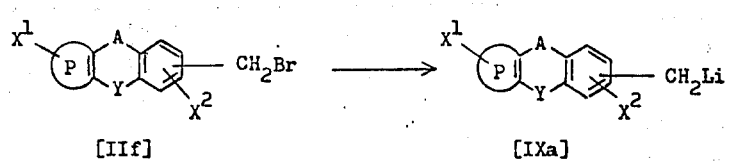

[IIf] → [IXa]

[IIf] is allowed to react with butyl-lithium in tetrahydrofuran to give [IXa].

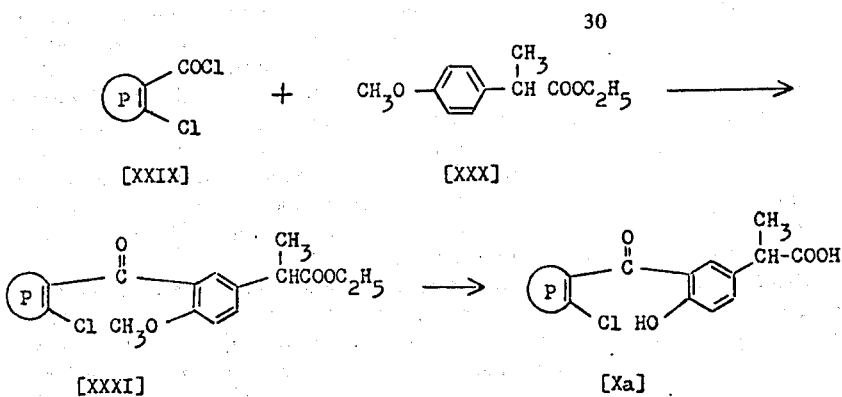

[XXIX] + [XXX] →

[XXXI] → [Xa]

Reaction of [XXIX] with [XXX] in dichloroethane in the presence of stannic chloride gives [XXXI]; [XXXI] is hydrolyzed to [Xa].

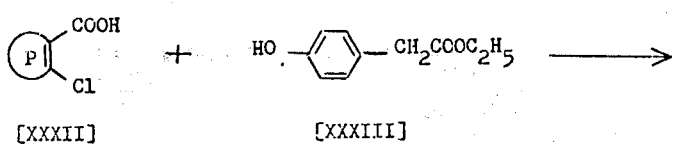

[XXXII] + [XXXIII] →

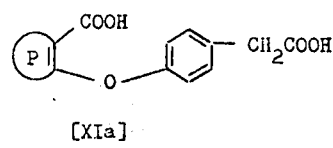

[XIa]

[XXXII] is heated with [XXXIII] at 160°–170°C to give [XIa].

The compounds of formula [I] wherein Z is OH can be converted in a conventional manner into the corresponding metal salts (the metal being for example Na, K, Ca, Mg or Al), the corresponding ammonium salts or the corresponding addition salts with organic bases such as triethylamine, diethylamine, morpholine or piperazine, and the compound of formula [I] wherein Z is Q—B—N($R^3$)($R^4$) can be converted in a conventional manner into the corresponding acid addition salts with various inorganic or organic acids such as hydrochloric, hydrobromic, sulfuric, phosphoric, nitric, methanesulfonic, p-toluenesulfonic, acetic, oxalic, maleic, fumaric, citric or camphorsulfonic acid.

The compounds of formula [I] and pharmaceutically acceptable salts thereof have analgesic and anti-inflammatory actions as shown, for example, by the following tests; in which the alphabetical notations A to D mean the following compounds, respectively:

A: 2-(5H-[1]benzopyrano[2,3-b]pyridin-7-yl)propionic acid,
B: 2-(5H-[1]benzothiopyrano[2,3-b]pyridin-7-yl)propionic acid,
C: 2-(5H-[1]benzopyrano[2,3-b]pyridin-7-yl)butyric acid,
D: 2-dimethylaminoethyl 2-(5H-[1]benzopyrano[2,3-b]pyridin-7-yl)propionate hydrochloride.

ANTI-INFLAMMATORY ACTION i. Carrageenin Edema Method

According to the method of Winter et al. (*Proc. Soc. Exptl. Biol. Med.*, 111, 544 (1962)), to one group of 5 Donryu-strain male rats each weighing about 130 g a test solution containing a test compound was administered orally. One hour later 0.05 ml of 1% carrageenin solution as a phlogogenic substance was subcutaneously injected to the paw of the hind leg. And 2 hours after the administration of phlogogen the bulk of the paw was measured in order to obtain the increment percentage over that before administration. The ratio of bulk increment between a control group and a test group was calculated as inhibition percentage.

ii. Ultraviolet Erythema Method

Using guinea pigs weighing 250–450 g, a rubber plate with 3 holes of 7 mm in diameter was fitted to the abdomen, hair of which had been removed in advance, and light was given by a mercury lamp (300 W, Tokyo Shibaura Electric Co., Ltd.) at the distance of 15 cm for 150 seconds. Two hours later the degree of erythema formation was marked according to the method of Winder et al. (*Arch. Intern. Pharmacodyn.*, 116, 261 (1958)) and the efficacy rate was calculated, based on the criterion that 1.5 or less of total marks be effective. Half amount of the test solution was orally given 1 hour before and after the irradiation.

ANALGESIC ACTION (PHENYQUINONE METHOD)

According to the method of Hendershot et al. (*J. Pharmacol. Exptl. Therap.*, 125, 237 (1957)), to one group of 6 dd-strain male mice each weighing about 20 g a test solution containing a test compound was orally administered and one hour later 0.2 ml/20 g of body weight of 0.02% o-phenyl-p-benzoquinone solution was intraperitoneally injected. The frequency of stretch symptoms thus induce was measured for 30 minutes, and compared with that of a control group, and the inhibition percentage (effect) was calculated.

Results:

Carrageenin Edema Method

| Compound | Dose mg/kg p.o. | % inhibition |
| --- | --- | --- |
| A | 1 | 58 |
|   | 3 | 61 |
| B | 1 | 32 |
|   | 3 | 60 |
| C | 10 | 48 |
|   | 30 | 70 |
| D | 5 | 23 |
|   | 10 | 57 |
| Aspirin | 30 | 15 |
|   | 100 | 52 |
| Phenylbutazone | 10 | 10 |
|   | 30 | 56 |

Ultraviolet Erythema Method

| Compound | Dose mg/kg p.o. | Animals with score of 1.5 or less / Total animals at 2 hr |
| --- | --- | --- |
| A | 0.05 | 2/5 |
|   | 0.25 | 7/10 |
| B | 0.05 | 2/5 |
|   | 0.5 | 3/5 |
| C | 1 | 1/5 |
|   | 2.5 | 3/5 |
| D | 0.5 | 1/5 |
|   | 1 | 3/5 |
| Aspirin | 50 | 1/10 |
|   | 100 | 4/10 |
| Phenylbutazone | 5 | 3/10 |
|   | 10 | 6/10 |

Phenylquinone Method

| Compound | Dose mg/kg p.o. | % inhibition |
| --- | --- | --- |
| A | 1 | 26.7 |
|   | 2.5 | 59.4 |
| B | 5 | 32.7 |
|   | 10 | 63.1 |
| C | 5 | 61.0 |
| D | 5 | 65.1 |
|   | 25 | 80.0 |
| Aspirin | 100 | 29.3 |
|   | 250 | 62.9 |
| Phenylbutazone | 100 | 37.2 |
|   | 250 | 55.4 |

In view of various tests including those mentioned above, the compounds of formula [I] in accordance with the invention and pharmaceutically acceptable salts thereof can be administered safely as anthirheumatics, analgesics, antipyretics and anti-inflammatory agents, either alone or in the form of a pharmaceutical composition consisting essentially of a therapeutically effective amount of the compound in admixture with a suitable and conventional carrier or adjuvant, administrable orally, percutaneously or by way of injection, without harm to the host.

The pharmaceutical composition can take the form of tablets, granules, powder or capsules, for oral administration, of injectable solution for subcutaneous or intramuscular administration, or of cream, ointment, jelly or suppository for topical administration. The choice of carrier is determined by the preferred form of administration, the solubility of the compounds and standard pharmaceutical practice.

The following is an example of formulations when a compound of the invention is administered for pharmaceutical purposes: 25 mg capsules are prepared from the following composition:

| 25 mg capsules are prepared from the following composition: | |
| --- | --- |
| Compound [A] | 25 mg |
| Lactose | 37 |
| Microcrystalline cellulose | 18 |
| Corn starch | 7 |
| Talc | 13 |
|  | 100 mg |

| 25 mg tablets are prepared from the following composition: | |
| --- | --- |
| Compound [A] | 25 mg |
| Lactose | 45 |
| Talc | 4.4 |
| Microcrystalline cellulose | 31.2 |
| Corn starch | 18.5 |
| Magnesium stearate | 0.9 |
|  | 125.0 mg |

The tablets may be sugar-coated in a conventional manner.

The usual daily dose of compound [A] or a salt thereof lies in the range of about 50–100 milligrams per human adult.

The present invention is further explained by way of the following illustrative examples.

EXAMPLE 1

A solution of 11.5 g of 7-cyanomethyl-5H-[1]benzopyrano[2,3-b]-pyridine in a mixture of 60 ml of acetic acid and 25 ml of concentrated hydrochloric acid is heated under reflux for 24 hours. After concentration, water is added to the residue, and further 10% sodium hydroxide solution is added to dissolve the residue. An insoluble material is removed by extraction with chloroform. The aqueous layer is made acid with acetic acid, and the resulting crystalline precipitate is filtered off. The crystals are recrystallized from dioxane to give 8.5 g of 5H-[1]benzopyrano[2,3-b]-pyridin-7-yl-acetic acid as white needles melting at 218°C.

The above objective compound can also be produced from 7-acetyl-5H-[1]benzopyrano[2,3-b]pyridine. Namely, the acetyl compound is subjected to Willgerodt reaction, and the thioamide compound obtained is hydrolyzed with potassium hydroxide in isopropyl alcohol.

The starting compound 7-cyanomethyl-5H-[1]benzopyrano[2,3-b]pyridine is prepared as follows:

5-Hydroxy-5H-[1]benzopyrano[2,3-b]pyridine is prepared from 5-oxo-5H-[1]benzopyrano[2,3-b]pyridine by the method described in *Journal of the Chemical Society*, 1952, pages 2057–62.

A mixture of 10 g of 5-hydroxy-5H-[1]benzopyrano[2,3-b]pyridine, 100 ml of isopropyl alcohol and 10 ml of 20% hydrochloric acid in isopropyl alcohol is refluxed for 3 hours, and the reaction mixture is allowed to stand overnight. The isopropyl alcohol is distilled off under reduced pressure, an aqueous carbonate solution is added to the residue, and then the mixture is extracted with chloroform. The chloroform layer is dried, and the chloroform is distilled off. The residue is recrystallized from isopropyl alcohol to give 7.5 g of 5H-[1]benzopyrano[2,3-b]pyridine as white crystals melting at 87°–88°C.

Hydrogen chloride gas is passed through a mixture of 10 g of 5H-[1]-benzopyrano[2,3-b]pyridine, 1.4 g of paraformaldehyde, 110 ml of concentrated sulfuric acid and 22 ml of concentrated hydrochloric acid at 80°C for 12 hours, while 2 g of paraformaldehyde is added in several portions to the reaction mixture. The reaction mixture is poured into water, and the whole mixture is neutralized with sodium carbonate, and extracted with a large amount of chloroform. The chloroform layer is dried, concentrated to 30 ml, and cooled. The resulting crystalline precipitate is filtered off, and recrystallized from chloroform to give 7-chloromethyl-5H-[1]benzopyrano[2,3-b]pyridine melting at 172°–174°C.

A solution of 7.8 g of potassium cyanide in 20 ml of water is added dropwise to a mixture of 23 g of 7-chloromethyl-5H-[1]benzopyrano[2,3-b]-pyridine and 200 ml of dimethylformamide. The mixture is allowed to stand at 55°–60°C for 2 hours, and then poured into a large amount of water. The resulting crystalline precipitate is filtered off, washed with water, and recrystallized from aqueous dioxane to give 20 g of 7-cyanomethyl-5H-[1]-benzopyrano[2,3-b]pyridine melting at 166°–167°C.

EXAMPLE 2

A solution of 12 g of 7-cyanomethyl-5-oxo-5H-[1]benzopyrano[2,3-b]-pyridine in a mixture of 60 ml of acetic acid and 25 ml of concentrated hydrochloric acid is heated under reflux on an oil bath for 24 hours. After concentration, water is added to the residue, and further a 10% sodium hydroxide solution is added to dissolve the residue. An insoluble material is removed by extraction with chloroform. The aqueous layer is made acid with acetic acid, and the resulting crystalline precipitate is filtered off and recrystallized from aqueous dimethylformamide to give 8.6 g of 5-oxo-5H-[1]benzopyrano[2,3-b]pyridin-7-yl-acetic acid as white needles melting at 244°–245°C.

The above objective compound can also be produced from 7-acetyl-5-oxo-5H-[1]benzopyrano[2,3-b]pyridine. Namely, the acetyl compound is subjected to Willgerodt reaction, and the thioamide compound obtained is hydrolyzed with potassium hydroxide in isopropyl alcohol.

The starting compound 7-cyanomethyl-5-oxo-5H-[1]benzopyrano[2,3-b]-pyridine is prepared as follows:

A mixture of 42 g of 7-methyl-5-oxo-5H-[1]benzopyrano[2,3-b]pyridine, 36 g of N-bromosuccinimide, 0.4 g of benzoyl peroxide and 420 ml of carbon tetrachloride is refluxed with stirring under ultraviolet light for 2 hours. The reaction mixture is filtered rapidly while it is hot. The crystals thus obtained are suspended in hot water (about 60°C). The suspension is stirred thoroughly, and filtered. The crystals are recrystallized from dioxane to give 47.1 g of 7-bromomethyl-5-oxo-5H-[1]benzopyrano[2,3-b]-pyridine melting at 211°–212.5°C.

To a mixture of 25 g of 7-bromomethyl-5-oxo-5H-[1]benzopyrano-[2,3-b]pyridine and 175 ml of dimethylformamide is added 5.1 g of sodium cyanide under ice cooling. The mixture is stirred at room temperature for 2 hours, and then 300 ml of water is added to the reaction mixture. The resulting crystalline precipitate is filtered off, washed with water, and recrystallized from dioxane to give 17 g of 7-cyanomethyl-5-oxo-5H-[1]-benzopyrano[2,3-b]pyridine melting at 198°–201°C.

EXAMPLE 3

A mixture of 3 g of ethyl 2-(5H-[1]benzothiopyrano[2,3-b]pyridin-7-yl)propionate and 0.48 g of sodium hydroxide is dissolved in a mixture of 25 ml of ethanol and 5 ml of water, and the solution is heated under reflux for 1.5 hours. The ethanol is distilled off under reduced pressure, and water is added to the residue. The mixture is made acid with acetic acid, and the crystalline precipitate is filtered off and recrystallized from aqueous dioxane to give 2.4 g of 2-(5H-[1]benzothiopyrano[2,3-b]pyridin-7-yl)propionic acid melting at 203°–204°C.

EXAMPLE 4

A mixture of 3.1 g of ethyl 2-(5-oxo-5H-[1]benzothiopyrano[2,3-b[-pyridin-7-yl)propionate and 0.48 g of sodium hydroxide is dissolved in a mixture of 25 ml of ethanol and 5 ml of water. The solution is heated under reflux for 1 hour. The ethanol is distilled off under reduced pressure, and the residue is dissolved in water.

The solution is made acid with acetic acid, and the crystalline precipitate is collected by filtration and recrystallized from aqueous dioxane to give 2.5 g of 2-(5-oxo-5H-[1]benzothiopyrano[2,3-b]pyridin-7-yl)propionic acid as pale yellowish white crystals melting at 206.5°–207.5°C.

EXAMPLE 5

A mixture of 100 g of ethyl 2-cyano-2-2-(5H-[1]benzopyrano[2,3-b]-pyridin-7-yl)propionate, 500 ml of glacial acetic acid and 200 g of concentrated hydrochloric acid is refluxed for 48 hours. The reaction mixture is concentrated, and the residue is dissolved in hot water. The solution is adjusted to pH 2–3 by addition of 10% sodium hydroxide. The resulting crystalline precipitate is washed thoroughly with water, and recrystallized from aqueous dioxane to give 74 g of 2-(5H-[1]benzopyrano[2,3-b]pyridin-7-yl)propionic acid as white crystals melting at 183°–183.5°C.

The starting compound ethyl 2-cyano-2-(5H-[1]benzopyrano[2,3-b]-pyridin-7-yl)propionate is prepared as follows:

A solution of 0.76 g of metallic sodium in 15 ml of ethanol is added to a mixture of 6.6 g of 7-cyanomethyl-5H-[1]benzopyrano[2,3-b]pyridine and 46 ml of diethyl carbonate, and the whole mixture is refluxed for 1 hour. After cooling, 5.2 g of methyl iodide is added to the reaction mixture. The temperature of the mixture is raised gradually, and the mixture is refluxed for 2 hours. The excess diethyl carbonate is distilled off, and toluene is added to the residue. The mixture is washed with water, and the toluene layer is dried. The toluene is distilled off, and the residue is recrystallized from isopropyl alcohol to give ethyl 2-cyano-2-(5H-[1]benzopyrano-[2,3-b]pyridin-7-yl)propionate melting at 119°–120°C.

EXAMPLE 6

A mixture of 16.5 g of ethyl 2-cyano-2-(5-oxo-5H-[1]benzopyrano-[2,3-b]pyridin-7-yl)propionate, 80 ml of acetic acid and 35 ml of concentrated hydrochloric acid is heated under reflux for 24 hours. After concentration, water is added to the residue, and further a 10% sodium hydroxide solution is added to dissolve the residue. An insoluble material is removed by extraction with chloroform. The aqueous layer is made acid with acetic acid, and the crystalline precipitate is collected and recrystallized from aqueous dioxane to give 11 g of 2-(5-oxo-5H-[1]benzopyrano[2,3-b]pyridin-7-yl)propionic acid as white needles melting at 194°–195°C.

The starting compound ethyl 2-cyano-2-(5-oxo-5H-[1]benzopyrano-[2,3-b]pyridin-7-yl)propionate is prepared as follows:

A solution of 0.75 g of metallic sodium in 16 ml of ethanol is added to a mixture of 7 g of 7-cyanomethyl-5-oxo-5H-[1]benzopyrano[2,3-b]-pyridine and 55 ml of diethyl carbonate with stirring, and the mixture is stirred under reflux for 2 hours. After ice cooling, a solution of 5.2 g of methyl iodide in 5 ml of ethanol is added to the reaction mixture, and the whole mixture is stirred under reflux for 2 hours. The ethanol and the excess diethyl carbonate are distilled off under reduced pressure, and the residue is dissolved in toluene. The solution is washed with water, dried over anhydrous sodium sulfate, and concentrated under reduced pressure to give 8.4 g of crude crystals of ethyl 2-cyano-2-(5-oxo-5H-[1]benzopyrano-[2,3-b]pyridin-7-yl)propionate. The product, when recrystallized from isopropyl alcohol, melts at 106°–108°C.

EXAMPLE 7

2.4 g of 2-(5H-[1]benzopyrano[2,3-b]pyridin-7-yl)propionaldehyde is added in small portions to a mixture of 2.5 g of silver oxide, 50 ml of water, 50 ml of ethanol and 1.6 g of sodium hydroxide under cooling. The mixture is stirred for 30 minutes, and the silver produced is removed by filtration, and then the ethanol is distilled off. Water is added to the residue, and the resulting mixture is filtered to remove an insoluble material. The filtrate is adjusted to pH 3–4 by addition of hydrochloric acid. Thus 1.8 g of 2-(5H-[1]benzopyrano[2,3-b]pyridin-7-yl)propionic acid is obtained as precipitate. The product, when recrystallized from aqueous dioxane, melts at 182°–183°C.

EXAMPLE 8

1.6 G of potassium permanganate is added in small portions to a mixture of 2.5 g of 2-(5-oxo-5H-[1]benzopyrano[2,3-b]pyridin-7-yl)propionaldehyde, 20 ml of pyridine and 30 ml of water under cooling. The mixture is stirred at room temperature for 1 hour, and the manganese dioxide produced is removed by filtration. The filtrate is concentrated, and the residue is dissolved in water. The solution is treated with an activated charcoal, and made acid with hydrochloric acid to yield a precipitate of 2-(5-oxo-5H-[1]benzopyrano[2,3-b]pyridin-7-yl)propionic acid. The product, when recrystallized from aqueous dioxane, melts at 193°–194°C.

EXAMPLE 9

4.75 g of 2-(5-oxo-5H-[1]benzopyrano[2,3-b]pyridin-7-yl)propionic acid is dissolved in a solution of 0.88 g of sodium hydroxide in 25 ml of water. To the solution are added 5 g of sodium borohydride and a small amount of toluene, and the mixture is heated under reflux for 3 hours. The reaction mixture is adjusted to pH 3 by adding concentrated hydrochloric acid under ice cooling. The resulting crystalline precipitate is filtered off, washed with water, and recrystallized from aqueous dioxane to give 2.5 g of 2-(5H-[1]benzopyrano[2,3-b]pyridin-7-yl)propionic acid as white needles melting at 182.5°–183.5°C.

EXAMPLE 10

A mixture of 3.7 g of zinc, 0.22 g of mercuric chloride, 0.22 ml of concentrated hydrochloric acid and 3.7 ml of water is stirred for 5 minutes, and the aqueous solution is removed by decantation. To the zinc amalgam thus obtained are added 6 ml of dioxane and 6 ml of concentrated hydrochloric acid. 1.5 g of 2-(5-oxo-5H-[1]benzothiopyrano[2,3-b]pyridin-7-yl)propionic acid is added to the mixture with stirring at 50°–60°C over a period of about 15 minutes. The whole mixture is stirred at 60°C for 1 hour. The excess zinc is removed by filtration, and the filtrate is evaporated under reduced pressure. The residue is dissolved in water, and the solution is adjusted to pH 2–3 by addition of 10% sodium hydroxide. The resulting crystalline precipitate is filtered off, and recrystallized from aqueous dioxane to give 0.8 g of 2-(5H-[1]benzothiopyrano[2,3-b]pyridin-7-yl)propionic acid as pale yellowish white crystals melting at 203°–204°C.

EXAMPLE 11

2.5 g of 2-(5H-[1]benzopyrano[2,3-b]pyridin-7-yl)acrylic acid is dissolved in 20 ml of 0.5 N aqueous sodium hydroxide soution, and 1 g of Raney nickel is added. The solution is stirred in a hydrogen stream at ordinary pressure and temperature until absorption of 230 ml of hydrogen is attained. The Raney nickel is removed by filtration, and the filtrate is neutralized with hydrochloric acid. The resulting crystalline precipitate is filtered off, washed with water, and recrystallized from aqueous dioxane to give 1.8 g of 2-(5H-[1]benzopyrano[2,3-b]pyridin-7-yl)propionic acid melting at 183°–184°C.

EXAMPLE 12

A mixture of 2.9 g of 2-chloro-2-(5H-[1]benzopyrano[2,3-b]pyridin-7-yl)propionic acid, 40 ml of 0.5 N aqueous sodium hydroxide solution and 1 g of Raney nickel is stirred in a hydrogen stream at ordinary pressure and temperature, until absorption of 230 ml of hydrogen is attained. The RAney nickel is then filtered off, and the filtrate is neutralized with hydrochloric acid. The crystalline precipitate is filtered off, washed with water, and recrystallized from aqueous dioxane to give 1.5 g of 2-(5H-[1]benzopyrano-[2,3-b]pyridin-7-yl)propionic acid melting at 183°–184°C.

EXAMPLE 13

A Grignard reagent is prepared from 0.31 g of metallic magnesium and 2.9 g of 7-(1-bromoethyl)-5H-[1]benzopyrano[2,3-b]pyridine in 10 ml of anhydrous tetrahydrofuran. To the Grignard reagent is added a large excess of dry ice. The mixture is allowed to stand overnight, and then poured into diluted hydrochloric acid. The precipitate is filtered off, and added to an aqueous sodium bicarbonate solution. An insoluble material is removed by filtration, and the filtrate is made acid with acetic acid. The resulting white crystals are collected and recrystallized from aqueous dioxane to give 2-(5H-[1]benzopyrano[2,3-b]pyridin-7-yl)propionic acid melting at 182.5°–183.5°C.

EXAMPLE 14

2.5 g of 2-[3-(2-chloronicotinoyl)-4-hydroxyphenyl]propionic acid and 0.7 g of sodium hydroxide are dissolved in 10 ml of water. Catalytic amounts of powdered copper and copper iodide are added to the solution, and the mixture is stirred under reflux for 2 hours. After cooling, the reaction mixture is diluted with water, and filtered with suction. The filtrate is made acid with hydrochloric acid, and the resulting crystals are filtered off and recrystallized from aqueous dioxane to give 1.6 g of 2-(5-oxo-5H-[1]benzopyrano[2,3-b]pyridin-7-yl)propionic acid melting at 193.5°–194.5°C.

EXAMPLE 15

A mixture of 28.7 g of 2-(p-α-carboxyethylphenoxy)-nicotinic acid and 290 g of polyphosphoric acid is stirred at 130°–140°C on an oil bath for 1.5 hours. The reaction mixture is poured into ice water, and the precipitated crystals are collected by filtration. The crystals are washed with water, and recrystallized from aqueous dioxane to give 23.1 g of 2-(5-oxo-5H-[1]benzopyrano[2,3-b]pyridin-7-yl)propionic acid as white crystals melting at 194°–195°C.

EXAMPLE 16

A solution of 2 g of aluminum isopropoxide in 30 ml of isopropyl alcohol is added dropwise to a solution of 2.7 g of 2-(5-oxo-5H-[1]benzopyrano[2,3-b]pyridin-7-yl)propionic acid in 100 ml of isopropyl alcohol with stirring. The addition is accompanied by immediate formation of white crystals. The mixture is stirred under reflux for 1 hour, and 20 ml of water is added to the reaction mixture, and then the whole mixture is refluxed for an additional hour. After cooling, the crystals are filtered off, washed with isopropyl alcohol, and dried to give aluminum 2-(5-oxo-5H-[1]-benzopyrano[2,3-b]pyridin-7-yl)propionate as white crystals melting at above 250°C.

EXAMPLE 17

2.5 G of 2-(5H-[1]benzopyrano[2,3-b]pyridin-7-yl)propionic acid is dissolved in 80 ml of isopropyl alcohol. A solution of 2.1 g of aluminum isopropoxide in 25 ml of isopropyl alcohol is added dropwise to the solution with stirring, white crystals being immediately yielded. After refluxing the mixture for 1 hour, 3 ml of water is added, and then the whole mixture is further refluxed for 1 hour. After cooling, the crystals are filtered off, washed with isopropyl alcohol, and dried to give aluminum 2-(5H-[1]-benzopyrano[2,3-b]pyridin-7-yl)propionate as white crystals melting at above 250°C.

EXAMPLE 18

5.1 G of 2-(5H-[1]benzopyrano[2,3-b]pyridin-7-yl)propionic acid and 1.96 g of 2-dimethylaminoethanol are dissolved in 30 ml of pyridine. 4.2 g of p-tolylsulfonyl chloride is added in small portions to the pyridine solution with stirring at room temperature, and the mixture is stirred at 80°–90°C for 2 hours. The pyridine is distilled off under reduced pressure, and the residue is dissolved in chloroform. After addition of ice water, the solution is adjusted to pH 9 by addition of 15% sodium hydroxide. The mixture is thoroughly shaken, and the chloroform layer is separated. The chloroform layer is washed with water, dried over anhydrous magnesium sulfate, and concentrated. The residual oil is dissolved in 30 ml of isopropyl alcohol, and the solution is adjusted to pH 1–2 by addition of 20% alcoholic hydrochloric acid. After cooling, the crystalline precipitate is filtered off, and high vacuum dried to give 4.2 g of 2-dimethylaminoethyl 2-(5H-[1]benzopyrano[2,3-b]pyridin-7-yl)propionate hydrochloride melting at 167°–169°C.

EXAMPLE 19

A mixture of 6.1 g of ethyl 2-(5-oxo-5H-[1]benzothiopyrano[2,3-b]-pyridin-7-yl)propionate, 4 g of 2-dimethylaminoethanol, 0.3 g of sodium methyoxide and 100 ml of toluene is stirred under reflux for 6 hours, while the by-product ethanol is distilled off. As toluene also escapes during the ethanol distillation, the corresponding amount of toluene is replenished at appropriate intervals. After cooling, the reaction mixture is washed with water, dried over anhydrous magnesium sulfate, and concentrated. The residue is dissolved in isopropyl alcohol, and 20% alcoholic hydrochloric acid in isopropyl alcohol is added to the solution, and then the mixture is cooled with ice. The resulting crystalline precipitate is filtered off, and recrystallized from ethanol to give 5.3 g of 2-dimethylaminoethyl 2-(5-oxo-5H-[1]benzothiopyrano[2,3-b]pyridin-7-yl)propionate hydrochloride melting at 196°–198°C.

Using the procedure set forth in the above examples, but substituting equivalent amount of the appropriate starting materials, the following compounds are also produced.

1. 2-(5H-[1]benzopyrano[2,3-b]pyridin-7-yl)butyric acid, melting at 165°–167°C;
2. 2-(5H-[1]benzopyrano[2,3-b]pyridin-9-yl)propionic acid, melting at 196°–198°C;
3. 2-(5H-[1]benzopyrano[2,3-b]pyridin-7-yl)isobutyric acid, melting at 208°C;
4. 2-(2-methyl-5H-[1]benzopyrano[2,3-b]pyridin-7-yl)propionic acid, melting at 186°–187°C;
5. 2-(9-chloro-5H-[1]benzopyrano[2,3-b]pyridin-7-yl)propionic acid, melting at 196°–200°C;
6. 2-(2-methoxy-5H-[1]benzopyrano[2,3-b]pyridin-7-yl)propionic acid;
7. 2-(5H-[1]benzopyrano[2,3-b]pyridin-7-yl)propionic acid N-oxide, melting at 255°C with decomposition;
8. sodium 2-(5H-[1]benzopyrano[2,3-b]pyridin-7-yl)propionate, melting at above 300°C;
9. 2-(5-oxo-5H-[1]benzopyrano[2,3-b]pyridin-9-yl)propionic acid, melting at 208°–210°C;
10. 2-(5-oxo-5H-[1]benzopyrano[2,3-b]pyridin-7-yl)butyric acid, melting at 165°–166°C;
11. 2-(5oxo-5H-[1]benzopyrano[2,3-b]pyridin-7-yl)isobutyric acid, melting at 182°C;
12. 2-(2-methyl-5-oxo-5H-[1]benzopyrano[2,3-b]pyridin-7-yl)propionic acid, melting at 182°–184°C;
13. 2-(2-methoxy-5-oxo-5H-[1]benzopyrano[2,3-b]pyridin-7-yl)propionic acid;
14. 5-oxo-5H-[1]benzopyrano[3,2-c]pyridin-8-yl-acetic acid, melting at 275°C;
15. 2-(5-oxo-5H-[1]benzopyrano[2,3-b]pyridin-7-yl)propionic acid N-oxide, melting at 265°C with decomposition;
16. 5,5-dimethyl-5H-[1]benzopyrano[2,3-b]pyridin-7-yl-acetic acid, melting at 234°C;
17. 5-oxo-5H,10H-benzo[b][1,8]naphthyridin-7-yl-acetic acid, melting at 317°C;
18. 10-methyl-5-oxo-5H,10H-benzo[b][1,8]naphthyridin-7-yl-acetic acid, melting at 259°C;
19. 2-morpholinoethyl 2-(5H-[1]benzopyrano[2,3-b]pyridin-7-yl)propionate, $n_D^{24.5}$ = 1.5655
20. 2-(4-methyl-1-piperazinyl)ethyl 2-(5H-[1]benzopyrano[2,3-b]pyridin-7-yl)propionate, dihydrochloride, melting at 251°–252°C;
21. 3-piperidinopropyl 2-(5H-[1]benzopyrano[2,3-b]pyridin-7-yl)propionate, $n_D^{26}$ = 1.5598;
22. 2-dimethylaminoethyl 2-(5H-[1]benzothiopyrano[2,3-b]pyridin-7-yl)-propionate, $n_D^{26}$ = 1.5862;
23. 2-dimethylamino-1-methylethyl 2-(5-oxo-5H-[1]benzopyrano[2,3-b]-pyridin-7-yl)propionate hydrochloride, melting at 195°–196°C;
24. N-(2-dimethylaminoethyl)-2-(5H-[1]benzopyrano[2,3-b]pyridin-7-yl)-propionamide hydrochloride, melting at 204°–206°C.

1. A compound selected from the group consisting of

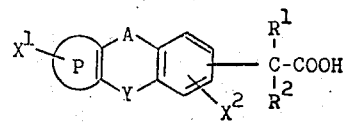

wherein each of $X^1$ and $X^2$ is a hydrogen atom, a halogen atom, an alkyl group having 1 to 4 carbon atoms or an alkoxy group having 1 to 4 carbon atoms; each of $R^1$ and $R^2$ is a hydrogen atom or an alkyl group having 1 to 4 carbon atoms; A is carbonyl, methylene or alkylidene having 2 to 4 carbon atoms; Y is —O—; and ring P represents a pyridine or pyridine N-oxide ring; and a pharmaceutically acceptable salt thereof.

2. A compound of claim 1:
5H-[1]benzopyrano[2,3-b]pyridin-7-yl-acetic acid.
3. A compound of claim 1:
2-(5H-[1]benzopyrano[2,3-b]pyridin-7-yl)propionic acid.
4. A compound of claim 1:
2-(5H-[1]benzopyrano[2,3-b]pyridin-9-yl)propionic acid.
5. A compound of claim 1:
2-(5H-[1]benzopyrano[2,3-b]pyridin-7-yl)butyric acid.
6. A compound of claim 1:
2-(5H-[1]benzopyrano[2,3-b]pyridin-7-yl)isobutyric acid.
7. A compound of claim 1:
2-(2-methyl-5H-[1]benzopyrano[2,3-b]pyridin-7-yl)propionic acid.
8. A compound of claim 1:
2-(9-chloro-5H-[1]benzopyrano[2,3-b]pyridin-7-yl)propionic acid.
9. A compound of claim 1:
2-(5H-[1]benzopyrano[2,3-b]pyridin-7-yl)propionic acid N-oxide.
10. A compound of claim 1:
5-oxo-5H-[1]benzopyrano[2,3-b]pyridin-7-yl-acetic acid.
11. A compound of claim 1:
2-(5-oxo-5H-[1]benzopyrano[2,3-b]pyridin-7-yl)propionic acid.
12. A compound of claim 1:
2-(5-oxo-5H-[1]benzopyrano[2,3-b]pyridin-9-yl)propionic acid.
13. A compound of claim 1:
2-(5-oxo-5H-[1]benzopyrano[2,3-b]pyridin-7-yl)butyric acid.
14. A compound of claim 1:
2-(5-oxo-5H-[1]benzopyrano[2,3-b]pyridin-7-yl)isobutyric acid.
15. A compound of claim 1;
10-oxo-10H-[1]benzopyrano[3,2-c]pyridin-8-yl-acetic acid.
16. a compound of claim 1:
2-(2-methyl-5-oxo-5H-[1]benzopyrano[2,3-b]pyridin-7-yl)propionic acid.
17. A compound of claim 1:
2-(5-oxo-5H-[1]benzopyrano[2,3-b]pyridin-7-yl)propionic acid N-oxide.
18. A compound of claim 1:
5,5-dimethyl-5H-[1]benzopyrano[2,3-b]pyridin-7-yl-acetic acid.

* * * * *